(12) United States Patent
Wong et al.

(10) Patent No.: US 6,544,958 B2
(45) Date of Patent: Apr. 8, 2003

(54) THERAPY OF RESPIRATORY INFLUENZA VIRUS INFECTION USING FREE AND LIPOSOME-ENCAPSULATED RIBONUCLEOTIDES

(75) Inventors: Jonathan P. H. Wong, Medicine Hat (CA); Leslie P. Nagata, Medicine Hat (CA)

(73) Assignee: Her Majesty the Queen in right of Canada, as represented by the Minister of National Defence of Her Majesty's Canadian Government, Ottawa (CA)

(*) Notice: Subject to any disclaimer, the term of this patent is extended or adjusted under 35 U.S.C. 154(b) by 0 days.

(21) Appl. No.: 09/816,138

(22) Filed: Mar. 26, 2001

(65) Prior Publication Data

US 2002/0136761 A1 Sep. 26, 2002

(51) Int. Cl.[7] ............................ C07H 21/00; C12Q 1/68
(52) U.S. Cl. .............................. 514/44; 435/6; 435/325; 435/375; 536/23.1; 536/24.5
(58) Field of Search ............................ 435/6, 325, 375; 514/44; 536/23.1, 24.5

(56) References Cited

U.S. PATENT DOCUMENTS 5,580,767 A * 12/1996 Cowsert et al. .......... 435/172.3

OTHER PUBLICATIONS

Karin Renneisen et al., Inhibition of Expression of Human Immunodeficiency Virus–1 in Vitro by Antibody–targeted Liposomes Containing Antisense RNA to the env Region, The Journal of Biological Chemistry, vol. 256, No. 27, pp. 16337–16342.*

Mizuta, T., et al, (1999) *Nature Biotechnology*, 17 (6), 583–587.

Saravolac, E.G., et al, (1996) *Antiviral Res.*, 29:199–207.

Wong, J.P., et al, (1994) *Immunology*, 81:280–284.

Kende, M., et al, (1985) *Antimirob. Agents Chemotherapy.*, 27:903–907.

Wong, J.P., et al, (1995) in *Liposomes in Biomedical Applications,* Harwood Academic Press, Amsterdam, the Netherlands, pp. 105–120.

Conely, J., et al, (1997), *Antimicrob. Agents Chemotherapy*, 41:1288–1292.

* cited by examiner

*Primary Examiner*—Andrew Wang
*Assistant Examiner*—James D. Schultz
(74) *Attorney, Agent, or Firm*—Nixon & Vanderhye P.C.

(57) ABSTRACT

The present invention relates to novel ribonucleotide oligonucleotides (RNOs) that are specifically designed to inhibit viral replication. The RNOs are capable of binding to both the negative and positive strands of influenza RNA segments, thereby inhibiting the virus' ability to produce various viral components, thus inhibiting viral propagation, and effectively killing the virus at the intracellular sites of infection in the respiratory tract. The RNOs provided may act independently, or in combination to optimize their antiviral activity. In addition, the RNOs provided may be formulated in liposomes, which facilitate their therapeutic delivery to intracellular sites of infection, and additionally increase antiviral efficacies.

12 Claims, 4 Drawing Sheets

THERAPY OF RESPIRATORY INFLUENZA VIRUS INFECTION USING FREE AND LIPOSOME-ENCAPSULATED RIBONUCLEOTIDES

FIELD OF THE INVENTION

The present invention relates to novel nucleotides, and more specifically, ribonucleotide oligonucleotides (RNOs) that are specifically designed to inhibit viral replication at the intracellular sites of infection in the respiratory tract. The RNOs are capable of binding to both the negative and positive strands of influenza RNA segments, thereby inhibiting the virus' ability to produce various viral components, and therefore inhibit viral propagation. The RNOs provided may be formulated in liposomes, which facilitate their therapeutic delivery to intracellular sites of infection, and additionally increase antiviral efficacies.

BACKGROUND OF THE INVENTION

Despite recent advances in antiviral therapy and vaccination; acute respiratory infections caused by influenza viruses are important causes of human mortality and morbidity worldwide. Although influenza viruses generally cause a mild malaise in healthy individuals, for the high-risk segments of the population, such as the elderly, the young, and individuals with underlying chronic illness, influenza and the complications resulting from secondary infections, can be life threatening. It is estimated that in the United States alone, more than 10,000 people die each year from influenza and complications from influenza.

DESCRIPTION OF THE RELATED ART

Vaccination, or immunoprophylaxis, using inactivated or killed whole virus is a widely used conventional preventative measure used to reduce the impact of influenza [Centers for Disease Control, *Prevention and control of influenza: recommendations of the Immunization Practices Advisory Committee Weekly Report*, 1991; 41 (RR-9) 1–5]. However, there are significant limitations and drawbacks in such an antiviral vaccination.

A major disadvantage with killed whole virus, or inactivated, influenza virus vaccinations is that they are ineffective against new virus variants that result from genetic changes, such as those changes that arise from antigenic shifts in the haemagglutinin (HA) protein resulting in variations from one HA subtype to another. In addition, because such virus vaccines are propagated in eggs, individuals or populations that are sensitive to eggs and egg products are unsuitable for such vaccination.

Another conventional preventative measure used to reduce or control the impact of influenza is chemoprophylaxis, or chemotherapy, with an influenza-specific antiviral drug, such as amantadine or rimantadine [Centers for Disease Control. *Prevention and control of influenza: recommendations of the Immunization Practices Advisory Committee Weekly Report*, 1991; 41 (RR-9) 1–5]. In addition, neuraminidase inhibitors have also been recently commercialized for the treatment of influenza.

There are however, limitations to the use of such anti-influenza drugs. In particular, anti-influenza drugs such as amantadine and rimantadine are only partially effective against influenza A viruses, and are essentially ineffective against B strains of the influenza virus. Moreover, there is a rapidly increasing number of influenza A viruses that are developing resistance to amantadine and rimantadine, whereby such antiviral drugs are becoming rapidly ineffective against these more resistant strains of influenza A virus [Bleshe, R. B., et al, (1989), *J. Infect. Dis.*, 159: 430–435].

Oligonucleotides are promising therapeutic agents that have been shown to be effective against cancer and infectious diseases. The prior art also includes the use of antisense deoxyribonucleotides to treat neoplastic and infectious diseases [Mizuta, T., et al, (1999) *Nature Biotechnology*, 17 (6), 583–587]. Oligonucleotides directed against a target gene or messenger RNA can result in the inhibition of transcription and/or translation of virus genetic material, thereby blocking the synthesis of key virus proteins required for virus propagation. However, such unmodified oligonucleotides are particularly susceptible to degradation by nucleases in the serum, thus limiting their therapeutic potential.

Liposomes are microscopic lipid vesicles and they have been used successfully as drug delivery systems to enhance the therapeutic effectiveness of a number of therapeutic agents against influenza infections, including antiviral antibodies [Wong, J. P., et al, (1994) *Immunology*, 81:280–284], interferon-gamma [Saravolac, E. G., et al, (1996) *Antiviral Res.*, 29:199–207] and ribavirin [Kende, M., et al, (1985) *Antimirob. Agents Chemotherapy.*, 27:903–907].

It is known to use antisense deoxyribonucleotide oligonucleotides (i.e. DNA molecules) to treat viral infections. In addition, the known antisense oligonucleotides are adversely restricted to gene targets.

The present invention seeks to overcome the obstacles encountered in the prior art and provides the use of novel ribonucleotides, and liposome encapsulated ribonucleotides for the treatment of viral infection, and in particular influenza virus infection. The use of liposomes in this invention allows not only for the oligonucleotides be protected by nuclease degradation, but also allows the oligonucleotides to be delivered to the intracellular sites of infection in the lungs, thereby resulting in enhancing their antiviral inhibition efficacy.

Thus, an object of the present invention is to provide ribonucleotide oligonucleotides (RNOs), either free, or encapsulated in liposomes for the prevention and treatment of viral infections. The use of RNOs offers several distinct advantages over antisense deoxyribonucleotides oligonucleotides. For example, influenza virus, which is an RNA virus, replicates itself by transcribing its RNA into mRNA and then proceeds to translate mRNA into viral proteins. Subsequent to such protein synthesis, the replication of the viral RNA takes place via a synthesis of the cRNA. Accordingly, the use of RNOs, provided according to the present invention, will allow for the binding of such RNOs to either the viral RNA, cRNA and/or mRNA, therefore allowing for the increased functional efficacy in the treatment and prevention of viral infection.

SUMMARY OF THE INVENTION

An object of the present invention is to provide a method for treating, preventing and/or controlling influenza virus infections.

A particular object of the present invention is to provide novel ribonucleotides (RNOs) sequences specifically designed to inhibit viral replication and proliferation at intracellular sites of infection.

Another object of the present invention is to provide novel RNOs specifically designed to inhibit influenza virus replication and proliferation at intracellular sites of infection.

The present invention provides a plurality of ribonucleotide oligonucleotides (RNOs) with specific sequences, which act individually or collectively as therapeutic agents in the treatment and prevention of viral infection, and more specifically, influenza viral infection.

Accordingly, one aspect of the present invention provides a ribonucleotide having the following sequence:

ribonucleotide JW-T1 represented by oligonucleotide sequence SEQ ID NO: 1;
ribonucleotide JW-T2 represented by oligonucleotide sequence SEQ ID NO: 2;
ribonucleotide JW-T3 represented by oligonucleotide sequence SEQ ID NO: 3;

Reference will also be made to the following negative control sequence:

ribonucleotide JW-T4 represented by oligonucleotide sequence SEQ ID NO: 4;

wherein RNO JW-T4 does not inhibit the virus, and is provided for use in control studies relating to the present invention.

In addition, the present invention provides a ribonucleotide sequence including any one of RNOs JW-T1, JW-T2, or JW-T3, or any equivalent sequence thereof, or any combination thereof. Therefore, the present invention is not limited by RNOs sequences JW-T1, JW-T2, or JW-T3 represented in SEQ ID NO: 1, SEQ ID NO: 2, and SEQ ID NO: 3, respectively, but embodies any equivalent sequences, and larger fragment sequences, that may be used in accordance with the preferred uses of the present invention.

A preferred embodiment of the present invention comprises the formulation of such RNOs, either individually, or in any combination thereof, into liposomes.

Although the RNOs of the present invention are preferably directed to the treatment of influenza viral infection, the invention contemplates the use of ribonucleotides for the prevention and treatment of all viral infections. More specifically, the specific RNOs provided in the present invention are directed to a preferred use of preventing and treating all viral infections wherein the virus comprises haemagglutinin or a haemagglutinin gene. More preferably, the specific RNOs of the present invention may preferably be used for the prevention and treatment of influenza viral infection.

Therefore, all viral infections that allow for the binding of the RNOs, namely, JW-T1, JW-T2, or JW-T3, or comprise any equivalent sequence thereof, or any other sequence comprising or incorporating such RNOs, whereby the binding of such sequences to a virus result in the inhibition of viral infection, are embodied in the additional uses of the present invention.

Moreover, the present invention also embodies any RNO sequence equivalent to the preferred RNO sequences of the present invention, namely, JW-T1, JW-T2, or JW-T3. For example, the present invention also comprises RNO sequences that are effectively equivalent to the preferred RNOs sequences provided, such that mutations or changes effected to such preferred RNOs to yield modified, but equivalent RNO sequences are included in the embodiments of the present invention.

Appropriately, RNO, when referred to herein, includes RNO sequences JW-T1, JW-T2, or JW-T3, or any equivalent sequence thereof, or any larger sequence comprising JW-T1, JW-T2, or JW-T3, or any equivalent sequence thereof.

The present invention thus provides novel RNOs which are effective as either sense and/or antisense oligonucleotide sequences, capable of binding either the plus strand and/or the negative strand of a virus, in particular an influenza virus, thereby inhibiting the virus' ability to replicate.

The genetic sequences of the novel RNOs provided are unique and distinct from previously described antisense oligonucleotides. Moreover, the present invention provides the use of ribonucleotides for the effective treatment of viral infections. The RNOs provided in the present invention may bind to either sense and/or antisense oligonucleotide sequences, binding either the plus strand and/or the negative strand of a virus. Therefore, the RNOs of the present invention may bind to viral RNA, viral mRNA, and/or viral cRNA, and therefore, allow for the exceptional inhibition of viral infection.

It is well known that haemagglutinin (HA) plays an important and essential role in the pathogenesis of influenza viral infection. Accordingly, in a preferred embodiment, the novel RNOs provided act as either sense and/or antisense oligonucleotides capable of binding to the haemagglutinin (HA) gene, thereby inhibiting HA gene transcription, and/or are capable of binding to the transcribed HA mRNA, thereby inhibiting HA protein synthesis, and/or are capable of binding to the HA protein of the influenza virus particle itself, thereby inhibiting the action of HA protein, and effectively inhibiting viral replication and proliferation.

In another embodiment of the present invention, the novel RNOs are formulated or encapsulated into liposomes, whereby the encapsulation of such therapeutic RNOs into liposomes facilitates the RNOs delivery to, and efficacy at, a site of infection.

Liposome encapsulation of RNOs provides additional benefits. For example, liposome encapsulation will facilitate delivery of the active compounds to the sites of infection. In addition, liposome encapsulation may be used to attenuate the potential toxicity of RNOs as well as potentiate their antiviral efficacy. Moreover, liposome encapsulation may also allow for a reduction in the dosage of such active compounds, thereby reducing any toxic or side effects that may develop due to high dosage concentrations.

According to preferred embodiments of the present invention, RNOs JW-T1, JW-T2, and JW-T3, or any oligonucleotide sequence comprising JW-T1, JW-T2, and JW-T3, or any equivalent sequence or compound thereof, may be encapsulated into liposomes, and preferably, into non-charged liposomes, such that their antiviral efficacies may be optimized. Anionic and cationic liposomes may be used for liposome encapsulation.

The present invention also comprises the use of individual antiviral RNOs, either free or liposome encapsulated, or combinations of antiviral RNOs, either free or liposome encapsulated, according to embodiments of the present invention, for the treatment of influenza viral infection, and more specifically, influenza A viral infection in mammals.

In addition, the present invention provides therapeutic formulations of such RNOs, either free or liposome encapsulated, wherein said formulations may be designed for aerosol delivery, or may be formulated into a pharmaceutical composition that may optimize or facilitate its use.

BRIEF DESCRIPTION OF THE DRAWINGS

Embodiments of the present invention will now be described, by way of example, with reference to the accompanying drawings, wherein.

DETAILED DESCRIPTION OF THE PREFERRED EMBODIMENTS

The present invention provides novel ribonucleotides (RNOs) sequences specifically designed to inhibit viral replication and proliferation at intracellular sites of infection. In particular, the present invention provides novel RNOs specifically designed to inhibit influenza virus replication and proliferation at intracellular sites of infection, such as in the lungs or respiratory tract.

Accordingly, the invention provides different ribonucleotide oligonucleotides (RNOs) with specific sequences. The sequences of the RNOs are defined as follows:

(a) ribonucleotide JW-T1 is represented by oligonucleotide sequence SEQ ID NO: 1;
(b) ribonucleotide JW-T2 is represented by oligonucleotide sequence SEQ ID NO: 2;
(c) ribonucleotide JW-T3 is represented by oligonucleotide sequence SEQ ID NO: 3;
(d) ribonucleotide JW-T4 is represented by oligonucleotide sequence SEQ ID NO: 4.

It should be noted that RNOs JW-T1, JW-T2, and JW-T3, either individually, or in any combination thereof, effectively bind to either or both positive and/or negative strands of viral RNA, and in effect inhibit the virus, whereas RNO JW-T4 is a negative control sequence used in control studies relating to the present invention.

In accordance with the present invention, the genetic sequences of the novel RNOs are unique and distinct from previously described antisense oligonucleotides. One skilled in the art will appreciate that the use of specific ribonucleotide sequences is significantly dissimilar to the use of antisense deoxyribonucleotide oligonucleotides. As such, the present invention teaches the use of ribonucleotides, and specific ribonucleotide sequences, for the treatment and prevention of infectious disease caused by RNA viruses, such as influenza viruses.

In accordance with the preferred embodiments of the present invention, RNOs JW-T1, JW-T2, and JW-T3 are ribonucleotide oligonucleotide sequences that can effectively bind to either, or both, positive and/or negative strands of viral RNA, and more particularly, influenza viral RNA. The binding of said RNOs will effectively inhibit the virus' ability to make the viral components, such as RNA, or proteins needed for viral replication and propagation, such that the RNOs effectively prevent viral proliferation, and in effect bring about viral death.

As mentioned above, JW-T4 is a ribonucleotide oligonucleotide sequence that is a negative control sequence that was used in studies relating to the present invention. Negative control sequence JW-T4 does not bind to the viral RNA strands, and does not affect, nor does it promote or inhibit viral transcription and/or translation. Therefore, negative control RNO sequence JW-T4 does not offer any protection against influenza viral infection.

Thus, according to an aspect of the present invention, RNOs JW-T1, JW-T2, and JW-T3, either individually, or in any combination thereof, act as therapeutic agents in the treatment of viral infection, and more specifically, influenza viral infection. For example, the binding of novel RNOs JW-T1, JW-T2, and/or JW-T3 to either the negative or positive strands of influenza RNA segments, will prevent either transcription or translation, or both processes, and accordingly will inhibit viral replication. The inhibition of the transcription and/or translation of influenza viral components, such as mRNA, and protein needed for viral propagation, effectively inhibits the propagation of the virus.

It should be noted that the present invention is not limited to the ribonucleotide oligonucleotide sequences of JW-T1, JW-T2, and JW-T3. An additional embodiment of the present invention comprises any oligonucleotide sequence comprising the sequence of JW-T1, JW-T2, and/or JW-T3, or any equivalent sequence thereof. Moreover, another embodiment in accordance with the present invention may comprise RNOs JW-T1, JW-T2, and/or JW-T3, or any oligonucleotide sequence comprising JW-T1, JW-T2, and/or JW-T3, or any equivalent sequence, that is conjugated to another molecule, which may facilitate or ameliorate the antiviral activities thereof. For example, such RNOs may be bound to a carrier molecule that will facilitate or ameliorate its antiviral activity, or enhance its delivery to the site of infection.

The ribonucleotide oligonucleotides of the present invention allow for the effective inhibition of viral replication and proliferation. The binding of such RNOs to the negative strand of the viral RNA allow for the effective inhibition of the transcription of the negative strand into the plus strand (mRNA). Moreover, the RNOs may additionally bind to the transcribed viral RNA (i.e. mRNA) thereby allowing for the effective inhibition of the translation of the viral mRNA. Therefore, the binding of the RNOs provided in effect inhibits viral replication and proliferation by essentially preventing viral transcription and/or translation and consequently inhibit viral protein synthesis.

Haemagglutinin (HA) plays an important and essential role in the pathogenesis of influenza viral infection in that it allows for the fusion of the virus particle to the host pulmonary epithelial cells, thereby enabling the viral genetic material to be delivered intracellularly to the host cells. Accordingly, the introduction of specific RNOs, and more specifically, non-phosphorotioate ribonucleotide oligonucleotides, that will bind to, or interact with, the sense and/or antisense strands encoding the HA gene, so as to specifically inhibit the transcription and/or translation of the HA gene, and therefore results in the inhibition of viral replication.

Therefore, according to a preferred embodiment, novel RNOs JW-T1, JW-T2, and JW-T3 may act as either sense and/or antisense oligonucleotides capable of binding to the haemagglutinin (HA) gene, thereby inhibiting HA gene transcription, and/or are capable of binding to the transcribed HA mRNA, thereby inhibiting HA protein synthesis, and/or are capable of binding to the HA protein of the influenza virus particle itself, thereby inhibiting the action of HA protein. Thus, the inhibition of the HA protein and its action will effectively result in the inhibition of viral replication.

The RNOs according to the present invention may be used to treat and/or prevent each type of influenza virus infection. Therefore, RNOs of the present invention are not limited to the treatment or prevention of influenza A, but may be used for the treatment and prevention of each type of influenza virus, such as influenza A, B and C. The ability of the RNOs of the present invention to inhibit influenza virus infection of various influenza virus strains is possible since such RNOs are directed to and target the haemagglutinin protein of the influenza virus.

Therefore, since haemagglutinin plays an important and essential role in the pathogenesis of influenza viral infection, such that the haemagglutinin protein is present as an envelope protein in influenza viruses, the binding of the RNOs of the present invention to the haemagglutinin gene or protein will, in effect, inhibit influenza virus infection. The RNOs JW-T1, JW-T2 and JW-T3, may act as either sense and/or antisense oligonucleotides capable of binding to the haemagglutinin (HA) gene, thereby inhibiting HA gene transcription, and/or are capable of binding to the transcribed HA mRNA, thereby inhibiting HA protein synthesis, and/or are capable of binding to the HA protein of the influenza virus particle itself, thereby inhibiting the action of HA protein, and effectively inhibiting viral replication and proliferation of all influenza viruses. Thus, the present invention is not limited to the treatment and prevention of infection due to influenza virus A, but provides for the treatment, prevention, and inhibition of influenza virus infection caused by any influenza virus strain.

Another aspect of the present invention is to facilitate and ameliorate the delivery and efficacies of the therapeutic antiviral formulations to the sites of infection. More specifically, in a preferred embodiment of the present invention, such novel therapeutic antiviral RNOs are formulated or encapsulated into liposomes, whereby the encapsulation of such RNOs into liposomes facilitates the RNOs delivery to, and efficacy at, the sites of infection.

Accordingly, in a preferred embodiment of the present invention, RNOs JW-T1, JW-T2, and JW-T3, either individually, or in any combination thereof, may be encapsulated into liposomes, which may enhance delivery of such therapeutic RNOs to the intracellular sites of infection. In addition, the formulation of such RNOs into liposomes may also allow for the reduction of the dosage of such compounds, thereby reducing any toxic or side effects that may develop due to high dosage concentrations.

Therefore, the present invention additionally embodies the encapsulation of specific antiviral sequences, namely provided RNOs, into liposomes. Liposome encapsulation of such compounds is additionally beneficial since the potential toxicity of the compounds is attenuated or diminished due to liposome encapsulation. Moreover, liposome encapsulation also facilitates the delivery of compounds to their appropriate sites of activity, such as to the sites of infection, while additionally protecting the encapsulated compounds from degradation, thereby potentiating and promoting their efficacies, such as their antiviral efficacies, at, for example, the sites of infection.

In accordance with preferred embodiments of the present invention, liposomes used to encapsulate the provided therapeutic RNOs are preferably non-charged liposome formulations. More specifically, preferred liposomes include remote loaded vesicles (RLVs), or multilamellar vesicles (MLVs), or any equivalent non-charged liposome formulation. Although, for example, cationic liposomes are not preferred, the present invention does not exclude the use of any liposome, such as anionic, cationic, or non-charged liposomes, which may potentially be suitable for the formulation of such RNOs so that their therapeutic efficacies may be enhanced, or so that their delivery to the sites of infection may be facilitated.

It should be noted that the formulation of therapeutic agents or drugs into liposomes may decrease the toxicities of the entrapped agents, while maintaining their efficacies. The encapsulation of the provided RNOs, or any therapeutic antiviral equivalent thereof, into liposomes will allow for the gradual and sustained release of the encapsulated agents, and will therefore avoid a rapid elevation of drug levels, and accordingly may reduce any adverse toxic effects. Moreover, since the encapsulation of the therapeutic agents into liposomes prevents and inhibits the dilution of such agents subsequent to administration, a reduced dosage may be used. In fact, the studies described below suggest that only approximately 10–20% of the dose of free unencapsulated RNOs is needed when administering encapsulated RNOs, while still maintaining the same level of protection achieved with the higher unencapsulated RNO dosages.

In addition, because liposomes are known to accumulate at sites of infection, and at tumour sites, liposomes provide optimum vehicles for the delivery of therapeutic compounds directed to the sites of infection. Accordingly, in preferred embodiments of the present invention, RNOs JW-T1, JW-T2, or JW-T3, or any oligonucleotide sequence comprising JW-T1, JW-T2, or JW-T3, or any equivalent sequence or compound thereof, are preferably encapsulated into liposomes, and preferably, into non-charged liposomes, such that their antiviral efficacies may be optimized.

An additional aspect of the present invention provides specific therapeutic antiviral, and more specifically, anti-influenza, agents formulated either as unencapsulated (free) RNOs, or liposome encapsulated RNOs, which are formulated for aerosol delivery. The formulation of the therapeutic RNOs according to the present invention for aerosol delivery will allow for the specific targeting of the therapeutic compounds directly to the primary sites of infection for influenza viruses, namely the lungs, and more specifically, the lower respiratory tract.

Moreover, the therapeutic compounds of the present invention may be formulated into pharmaceutical compositions that may optimize or facilitate their use. In particular, the compounds of the present invention may be formulated into pharmaceutical compositions for the effective treatment of antiviral infections, and more specifically, for the treatment of influenza viral infections. Such pharmaceutical compositions may comprise the free RNO or liposome encapsulated RNO, in association with a pharmaceutically acceptable carrier or diluent, and, if appropriate, any excipient or delivery facilitating agent. Thus, the RNOs of the present invention may be formulated into a pharmaceutical composition that may optimize or facilitate its use, and deployed in the form of a tablet drug, capsule, lozenge or liquid.

STUDIES RELATING TO THE INVENTION

The studies described below are provided to describe in detail some of the representative experimentations, including preferred methods and materials of the invention, and provide analysis of results and discussions thereon. These descriptions are provided for purposes of illustration of the inventive concepts, and are not intended to limit the scope of the invention as defined by the appended claims.

1.0 Materials and Methods 1.1 Ribonucleotide oligonucleotide synthesis and liposome preparation Oligonucleotides used in this study were prepared by Oligos Etc Inc. (Wilsonsville, Oreg., US). For all experiments, all RNOs were diluted in 0.9% sodium chloride made from RNAse-free water (Sigma, St. Louis, Mo.).

The sequences of the RNOs were as follows (SEQ ID NOs:1–4, respectively):

```
JW-T1   5' UCC CCU GCU UUU GCU 3'

JW-T2   5' AGC AAA AGC AGG GGA 3'

JW-T3   5' UCG UUU UCG UCC CCU 3'

JW-T4   5' UCG ACG UGC AGC UCG 3'   (negative control sequence)
```

As noted earlier, RNO JW-T4 is a negative control sequence that was used in studies relating to the present invention. Negative control sequence RNO JW-T4 does not offer any protection against viral infections, and influenza viral infection.

However, RNOs JW-T1, JW-T2, and JW-T3, either individually, or in any combination thereof, act as therapeutic agents in the treatment and prevention of viral infection, and more specifically, influenza viral infection. For example, the binding of JW-T1, JW-T2, and/or JW-T3 to either the negative or positive strands of influenza RNA segments, will prevent either transcription or translation, or both processes, and accordingly will inhibit or prevent viral replication and propagation.

The, RNOs JW-T1, JW-T2, and JW-T3 inhibit the influenza virus, in effect by binding to different regions of the influenza virus genome, and accordingly, RNOs JW-T1, JW-T2, and JW-T3 may display different functional efficacies with respect to viral inhibition. The relative functional efficacies of RNOs JW-T1, JW-T2, and JW-T3 with respect to viral inhibition may vary, with RNO JW-T2 exhibiting a greater relative efficacy than RNO JW-T1, while RNO JW-T1 exhibits a greater relative efficacy than RNO JW-T3. Nevertheless, RNOs JW-T1, JW-T2, and JW-T3 are each capable of effectively inhibition influenza virus infection.

It should be noted that the mechanisms of action effected by RNOs JW-T1, JW-T2, and JW-T3 are not restricted to the suppression and inhibition of viral replication. For example, influenza virus inhibition may be attributed to the inhibition of viral replication, but is not limited to such inhibition, and may include, for example, inhibition due to such RNOs effect as immunomodulators, wherein inhibition by such RNOs may be attributed to possible immunostimulation of humoral and cellular responses. Nevertheless, regardless of the mechanisms by which viral inhibition is effected, RNOs JW-T1, JW-T2, and JW-T3 are each capable of influenza virus infection, so as to prevent of treat such viral infection.

Moreover, since RNOs JW-T1, JW-T2, and JW-T3 each bind to different sites on the influenza viral RNA, the RNOs may be used independently, or in any combination thereof. The independent administration of an RNO according to the present invention is advantageously simple and is effective at preventing and treating influenza virus infection. However, a combination of such RNOs according to the present invention may also be used effectively. For example, combined administration of such RNOs may be used to inhibit viral infection caused by new variant and resistant strains of influenza virus.

The phospholipids and cholesterol used for the preparation of liposome-encapsulated RNOs were purchased from Avanti Polar Lipids (Alabaster, Ala.). Large multilamellar vesicles (MLVs) were prepared using phosphatidylcholine:cholesterol:phosphatidyl glycerol in a molar ratio of 7:2:1, and were prepared using the freeze-drying procedures described by Wong, J. P., et al [Wong, J. P., et al, (1995) in *Liposomes in Biomedical Applications,* Harwood Academic Press, Amsterdam, the Netherlands, pp. 105–120]. For the preparation of remote loaded vesicles (RLVs), RNOs were loaded into small 100 nm unilamellar vesicles using 400 mM ammonium sulfate concentration, as described by Conley, J., et al [Conely, J., et al, (1997), *Antimicrob. Agents Chemotherapy,* 41:1288–1292]. The lipid composition of the RLVs was 55:45 for phosphatidylcholine and cholesterol. It should be noted that the present invention is not limited by such specified preparations, and includes any suitable liposome formulation.

In addition to the encapsulation methods described above, RNOs may be encapsulated into liposome by the use of various suitable methods. For example, RNO encapsulated liposome formulations may be prepared using dehydration-rehydration, freeze-drying, remote loading or detergent dialysis techniques.

1.2 Mice

Six-week-old female BALB/c mice were obtained from the mouse breeding colony at Defence Research Establishment Suffield (DRES), Alberta, with the original breeding pairs purchased from Charles River Canada (St. Constant, Quebec). The use of these animals was reviewed and approved by Animal Care Committee at DRES. Care and handling of the mice followed guidelines set out by the Canadian Council on Animal Care.

1.3 Adaptation of influenza viruses in mice

Influenza A/PR/8 (H1N1) was passaged in mice as described by Wong, J. P., et al [Wong, J. P., et al, (1994) *Immunol.,* 81:280–284]. Influenza A/PR/8 virus was adapted in mice by four blind passages using egg-propagated virus (ATCC, Parklawn, Md.) as the initial inoculum. For each passage, five BALB/c mice, anaesthetized with sodium pentobarbital (50 mg/kg body weight, intraperitoneal), were inoculated intranasally with 50 µl of egg-propagated virus for the initial passage. At four days post infection, the mice were sacrificed and the lungs were aseptically removed. The lungs were subsequently homogenized in a tissue grinder with a mixture of 5 g sterile aluminum hydroxide powder and 10 ml phosphate buffered saline, pH 7.2, containing penicillin-G (100 µg/ml), fungizone (0.25 µg/ml) and streptomycin sulfate (100 µg/ml).

The lung homogenate was then centrifuged at 5,000×g for 15 minutes and the supernatant was used for re-inoculation into another 5 mice in subsequent passages. The supernatant from the fourth and final passage was inoculated into the allantoic cavity of embryonated hen's eggs and the eggs were incubated at 37° C. for 4–5 days. The allantoic fluids were then isolated and pooled. The pooled allantoic fluid was assayed by haemagglutination (HA) and by a mouse $LD_{50}$ assay. The HA assays were performed with 0.5% rooster erythrocytes (Institute Armand Frappier, Laval, PQ) by a standard technique [Grist N. R., et al., (1974), *Diagnostic methods in clinical virology,* Blackwell Scientific Publication, p. 103]. The HA titres of the supernatant from the ground lung extract from the fourth passage in mice, and from the allantoic fluid from the final passage in embryonated eggs were found to be 1:16 and 1:2,048, respectively.

1.4 Antiviral efficacy of free and liposome encapsulated RNOs

Free and liposomal encapsulated RNOs were administered to mice via intranasal (IN) instillation, where the volumes of inoculum used were 50 µl. For IN administration, mice were anaesthetized with sodium pentobarbital (50 mg/kg body weight, intraperitoneal). When the animals were unconscious, they were carefully supported by hands with their noses up, and the antiviral agents were gently applied with a micropipette into the nostrils. The applied volume was naturally inhaled into the lungs.

In the treatment of influenza A infection in mice, groups of sodium pentobarbital-anaesthetized mice (5–10 mice per group) were intranasally infected with 3 $LD_{50}$ of the mouse-adapted influenza A/PR/8 virus. At 8 and 24 hours post infection, the mice were treated with two intranasal doses of free, or liposome-encapsulated, RNOs (650 $A_{260}$ units/dose). The mice were then monitored daily for signs of influenza infection, and for changes in their body weights. At day 14 post virus infection, the number of mice which survived the virus challenge was then recorded.

1.4.1 Results of efficacy study of free and liposome encapsulated RNO's

The antiviral efficacies of free and liposome-encapsulated RNOs were evaluated using a lethal respiratory influenza A virus infection model in mice. It was demonstrated that the treatment of mice with specific RNOs and liposome encapsulated RNOs provide complete protection from a lethal respiratory influenza virus in these animals. For example, treatment with 675 $A_{260\ nm}$/ml, or with 34 $A_{260\ nm}$/mouse of oligonucleotide JW-T3 provides 100% protection from lethality through day 14 post infection in comparison to 100% mortality in the untreated control mice. It should be noted that the negative control sequence JW-T4 did not offer any protection.

The use of liposome encapsulated RNOs confers 100% protection from fatality as do the free RNOs, and additionally allows for a significant reduction in the total dosage required for the achievement of the same level of protection. More specifically, the total dosage of free RNOs may be reduced up to 80% when using liposome encapsulated RNOs. A dosage reduction, by way of liposome encapsulation, without a reduction in the efficacy and functionality of the RNO's administered is especially advantageous.

Therefore, the present study illustrates that RNOs and liposome encapsulated RNOs are both effective therapeutic agents for the treatment of respiratory influenza infection.

1.5 Statistics

The survival rates of control and treated mice were compared using the Mann-Whitney unpaired nonparametric one-tailed test (InStat, version 1.14; GraphPAD Software, San Diego, Calif.). Differences were considered statistically significant at $p<0.05$.

2.0 Results 2.1 Antiviral efficacy of RNOs and liposome encapsulated RNOs

Figure 1:
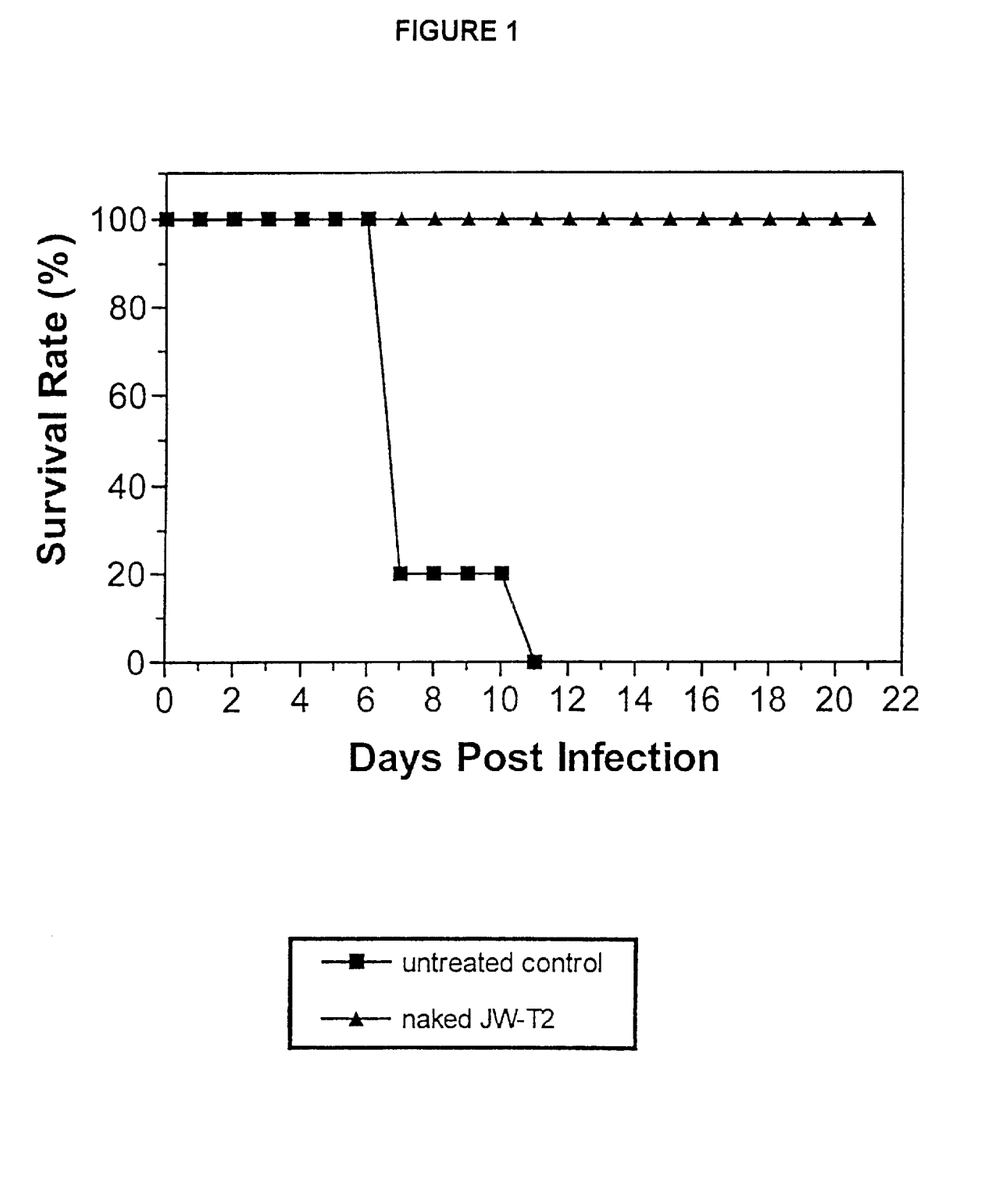
FIG. 1: is a graphical summary of the survival rate of untreated control mice and mice treated with unencapsulated (naked) JW-T2.
Figure 2:
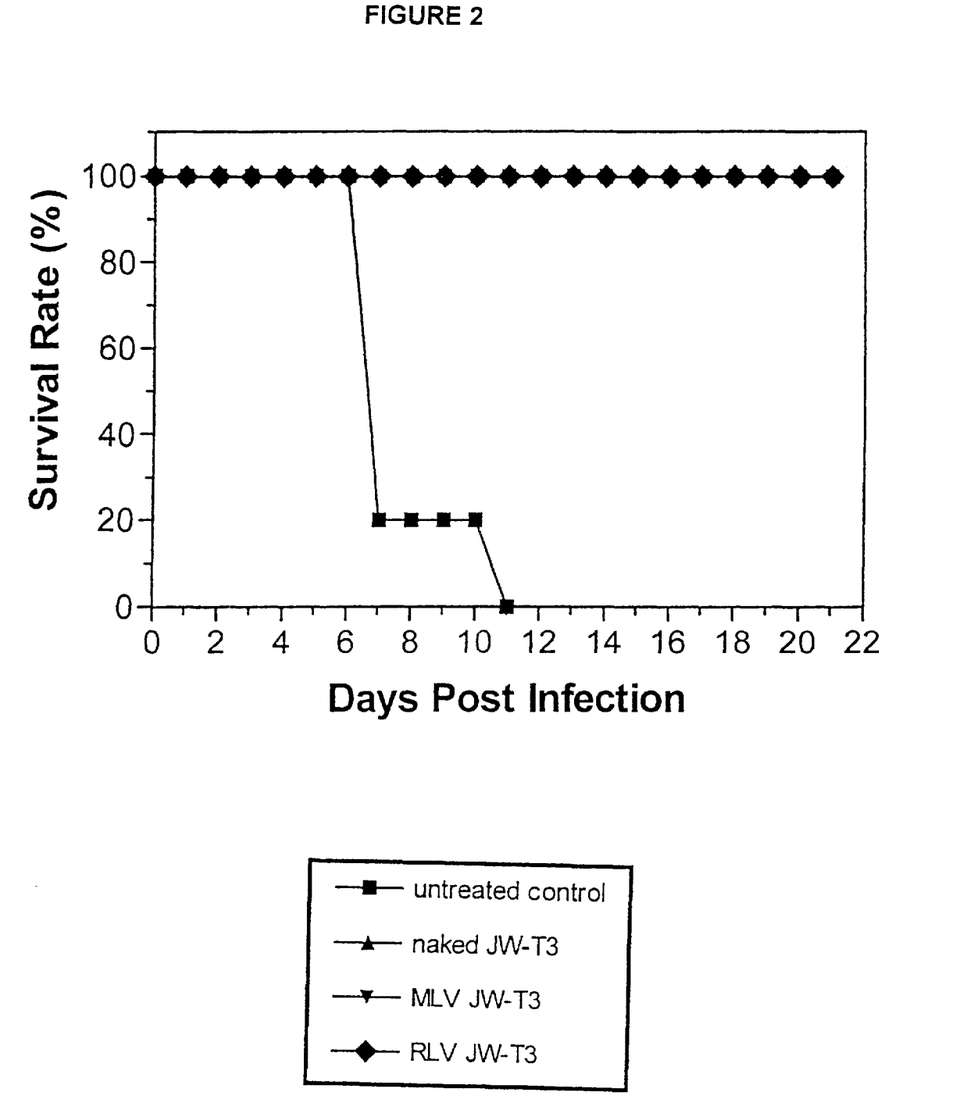
FIG. 2: is a graphical summary of the survival rate of untreated control mice and mice treated with unencapsulated (naked) JW-T3, and liposome encapsulated JW-T3.

The ability of RNOs and liposome encapsulated RNOs for the treatment of mice infected with otherwise lethal doses of influenza A/PR/8 virus is summarized in FIG. 1 and FIG. 2. As can be seen in both FIGS. 1 and 2, all untreated control mice, i.e. infected mice that were treated only with PBS, which is in effect a placebo, began to succumb to the virus challenge by day 6 post infection (20% survival rate), and all such untreated control animals were dead by day 11 post infection. In addition, it was also demonstrated that negative PBS treated control mice, that is infected mice that were treated with negative control RNO JW-T4 in PBS, also died from the virus challenge (data not shown).

Mice treated with two intranasal doses of JW-T2 (as seen in FIG. 1) and JW-T3 (as seen in FIG. 2) were fully protected, such that all mice in the treated groups survived the virus challenge at, and past, day 14 post infection (100% survival, $p<0.001$ vs. negative control). These treated animals were then monitored for another week and no death was observed. It should be noted that the treatment of infected mice with either JW-T1, JW-T2, or JW-T3 resulted in fully protected mice, that is to say, all mice in such treated groups survived the virus challenge at, and past, day 14 post infection.

Preliminary results suggest that liposome encapsulated JW-T3 was highly effective in the treatment of influenza virus infection in mice. Accordingly, it is estimated that the two intranasal liposome encapsulated JW-T3 (i.e. MLV JW-T3, and RLV JW-T3) doses administered were between 10%–20% of the dose of the free unencapsulated JW-T3 dose, and still maintained and provided the same level of protection (100%).

Figure 3:
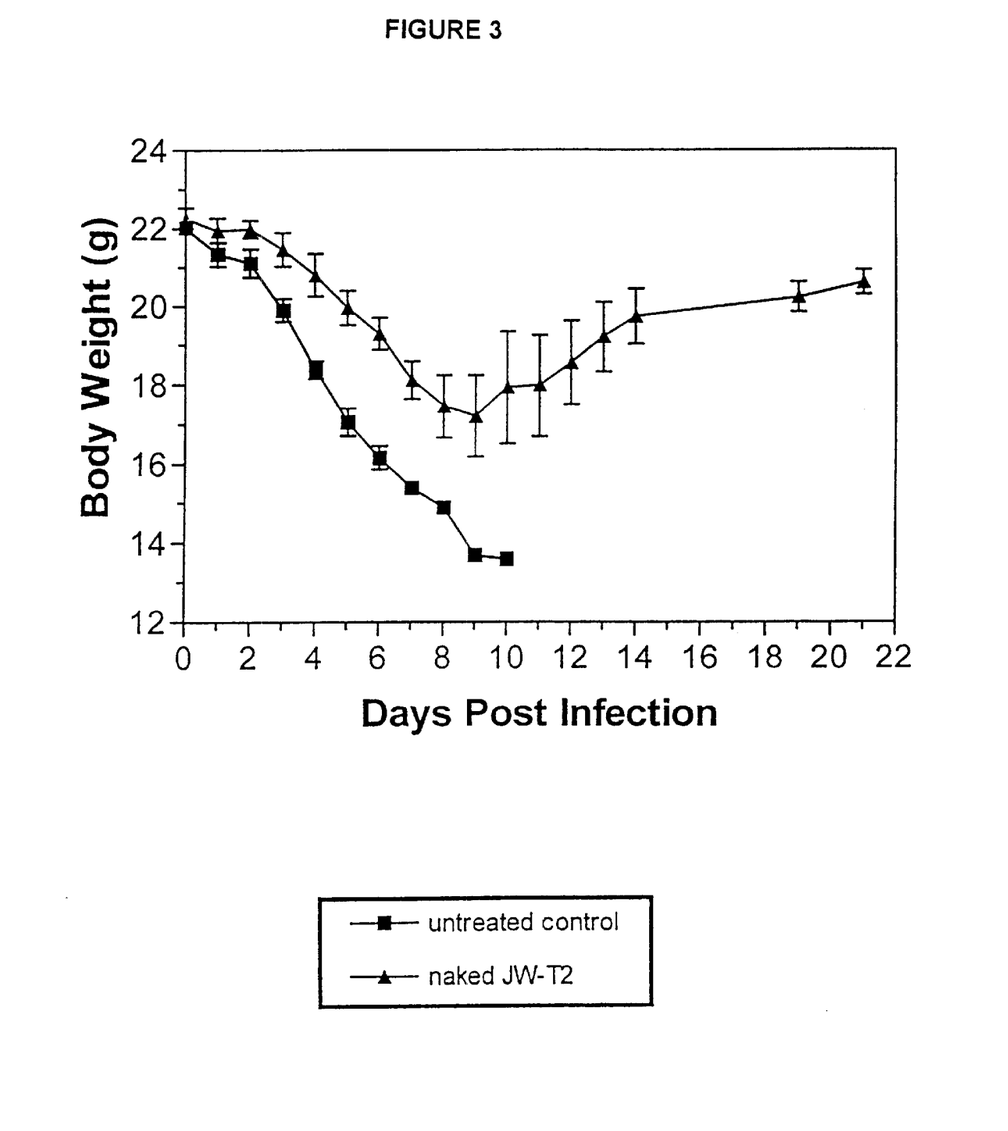
FIG. 3: is a graphical summary of the changes in body weight of untreated control mice and mice treated with unencapsulated (naked) JW-T2.
Figure 4:
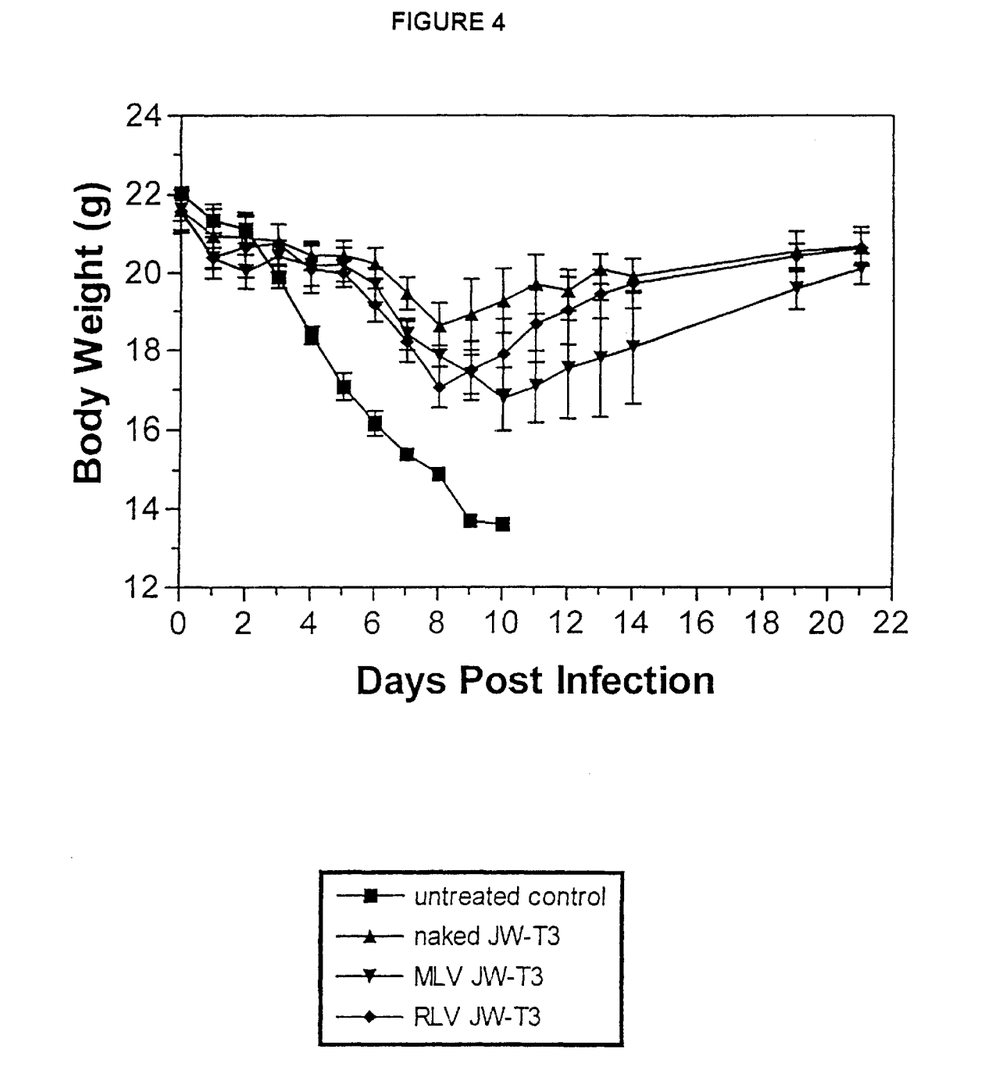
FIG. 4: is a graphical summary of the changes in body weight of untreated control mice and mice treated with unencapsulated (naked) JW-T3, and liposome encapsulated JW-T3.

When the body weights of the various groups of test and control mice were monitored, as illustrated in FIGS. 3 and 4, at various days post infection, all treated mice showed significantly less body weight loss resulting from the virus infection compared to the PBS negative control group, i.e. the untreated control group. There were no statistical differences between the body weights of animals treated with RNOs or RNOs in liposomes.

In addition, as can be seen from FIGS. 2 and 4, liposome-encapsulation did not appear to adversely affect the antiviral activity of RNOs. That is to say, the influenza infected mice that were treated with naked JW-T3 or with the liposome encapsulated JW-T3 were fully both protected, and survived the virus challenge at, and past, day 14 post infection (FIG. 2), and additionally exhibited significantly less body weight loss (FIG. 4).

3.0 Discussion

Prevention and treatment of influenza virus infection is becoming increasing problematic due to the ability of viruses to change their structures and to subsequently develop resistance to existing antiviral drugs, such as amantadine and rimantadine. As such, the requirement to develop new prophylactic and therapeutic approaches to prevent and treat influenza is becoming more compelling.

The use of antisense oligonucleotides to inhibit viral gene expression is becoming increasingly important. However, the use of conventional deoxyribonucleotide antisense oligonucleotides as therapeutic agents is limited by their high susceptibility to nuclease degradation in the body, and by their inability to cross cell membranes so as to penetrate intracellular sites of infection.

In addition, the use of such conventional deoxyribonucleotide antisense oligonucleotides involves the use of phosphorothioate oligonucleotides, which vary widely in efficacy for influenza therapy, ranging from 0–45% protection in mice [Mizuta, T., et al, (1999), *Nature Biotech.*, 17:583–587]. Accordingly, an advantage of the present invention involves the use of non-phosphorotioate ribonucleotide oligonucleotides, abbreviated RNOs, which are uniquely designed to specifically inhibit the transcription and translation of the HA gene.

In accordance with a preferred use, the RNOs of the present invention can either bind to the plus or negative strands of the influenza RNA. Moreover, in animal, i.e. mammalian studies, these RNOs demonstrated superior antiviral efficacy compared to that of conventional antisense oligonucleotides in the treatment of otherwise lethal influenza virus infection in mice. Therefore, the use of the RNOs and RNOs in liposomes, in accordance with the present invention, has resulted in complete (100%) protection of influenza infected treated mice, while negative control oligonucleotides provided no protection against the viral infection. It should be noted that the negative control oligonucleotides, such as JW-T4, do not specifically target the RNA strands of the influenza virus, and accordingly do not inhibit viral infection.

However, the novel RNOs provided in the present invention, namely JW-T1, JW-T2 and JW-T3, are specifically designed to bind to either the plus and/or negative strand of the influenza virus, and more specifically act on the haemagglutinin (HA) protein of the influenza virus, and accordingly inhibit replication and proliferation of all influenza viral strains comprising the haemagglutinin gene. Accordingly, it may be noted that the provided RNOs appear to suppress antiviral gene expression.

An additional use of the RNOs provided in accordance with the embodiments of the present invention may comprise the use of such RNOs in diagnostic or therapeutic applications. For example, RNOs according to the present invention may be used to diagnose the presence of a viral infection, using various diagnostic techniques, such as diagnostic PCR.

The use of liposomes as drug delivery systems for antimicrobial agents is becoming increasing important. The effectiveness of liposomes as carrier systems is primarily based on the ability of the liposomes to attenuate the toxicity of the entrapped drugs while maintaining their efficacies. Because of these characteristics, liposomes have much therapeutic potential as carriers for such drugs as antibiotics, antivirals, antifungals and anticancer agents. Liposomes can decrease the toxicities of entrapped drugs in a number of ways. Entrapped drugs may be released from the liposomes in a gradual and sustained manner, thereby avoiding rapid elevation of drug levels systemically. In addition, liposomes are known to accumulate at infection and tumour sites where the entrapped drugs are needed. Such accumulation may therefore concentrate the drugs at the sites or disease, thereby minimising the exposures of healthy organs and tissues to such drugs.

Appropriately, liposomes are used in the present invention so as to further enhance the antiviral activity of RNOs while reducing the drug toxicity. Increasing the RNOs antiviral efficacy by facilitating its delivery to the sites of infection, while additionally reducing any adverse toxic effects is exceptionally advantageous, and is an advantage that will facilitate the development of safer and more potent formulations of RNOs in various antiviral therapies.

Accordingly, an additional aspect of the present invention comprises the specific formulation of RNOs or liposome encapsulated RNOs for aerosol delivery to the lungs, and more specifically to the lower respiratory tract. This approach enables the specific targeting of RNOs or liposome encapsulated RNOs to the lungs, which are the primary infection sites for influenza viruses.

While preferred embodiments have been shown and described, it will be understood that there is no intent to limit the invention to such disclosure, but rather it is intended to cover all modifications and alternate constructions falling within the spirit and scope of the invention. It is therefore understood that, the present invention is not limited to the various embodiments described above, but encompasses any and all embodiments within the scope of the following claims.

We claim:

1. A ribonucleotide oligonucleotide (RNO) for treating influenza, comprising a sequence represented by SEQ ID NO: 1 or SEQ ID NO: 3.

2. A liposome comprising, encapsulated therein, at least one RNO, wherein said at least one RNO comprises a sequence represented by SEQ ID NO: 1 or SEQ ID NO: 3.

3. A formulation comprising a liposome of claim 2.

4. The formulation according to claim 3, wherein said liposome is an anionic, cationic or non-charged liposome.

5. The formulation according to claim 3, wherein said liposome is a remote loaded vesicle comprising phosphatidylcholine, cholesterol, and phosphatidyl glycerol in a molar ratio of 7:2:1.

6. The formulation according to claim 3, wherein said liposome is a multilamellar vesicle comprising phosphatidylcholine and cholesterol in a molar ratio of 55:45.

7. A pharmaceutical formulation comprising at least one RNO, wherein said at least one RNO comprises a sequence represented by SEQ ID NO: 1 or SEQ ID NO: 3, said formulation further comprising a pharmaceutically acceptable carrier, diluent, or delivery facilitating agent.

8. The pharmaceutical formulation according to claim 7, wherein the delivery facilitating agent is an aerosol.

9. A pharmaceutical formulation comprising a liposome of claim 2, and a pharmaceutically acceptable carrier, diluent or delivery facilitating agent.

10. The pharmaceutical formulation according to claim 9, wherein the delivery facilitating agent is an aerosol.

11. A method of treating influenza virus infection, or infections caused by viruses having a heamagglutinin gene, comprising administering the pharmaceutical formulation of claim 7, into an animal by intravenous, intranasal, intramuscular routes, or by aerosol inhalation.

12. A method of treating influenza virus infection, or infections caused by viruses having a heamagglutinin gene, comprising administering a formulation of claim 3, into an animal by intravenous, intranasal, intramuscular routes or by aerosol inhalation.

* * * * *

SEQUENCE LISTING

```
<160> NUMBER OF SEQ ID NOS: 4

<210> SEQ ID NO 1
<211> LENGTH: 18
<212> TYPE: RNA
<213> ORGANISM: Artificial Sequence
<220> FEATURE:
<223> OTHER INFORMATION: Description of Artificial Sequence:JW-T1

<400> SEQUENCE: 1 ucccugcug cuuuugcu                                                    18

<210> SEQ ID NO 2
<211> LENGTH: 15
<212> TYPE: RNA
<213> ORGANISM: Artificial Sequence
<220> FEATURE:
<223> OTHER INFORMATION: Description of Artificial Sequence:JW-T2

<400> SEQUENCE: 2
agcaaaagca gggga                                                      15

<210> SEQ ID NO 3
<211> LENGTH: 15
<212> TYPE: RNA
<213> ORGANISM: Artificial Sequence
<220> FEATURE:
<223> OTHER INFORMATION: Description of Artificial Sequence:JW-T3

<400> SEQUENCE: 3
```

-continued ucguuuucgu ccccu                                                    15

<210> SEQ ID NO 4
<211> LENGTH: 15
<212> TYPE: RNA
<213> ORGANISM: Artificial Sequence
<220> FEATURE:
<223> OTHER INFORMATION: Description of Artificial Sequence:JW-T4

<400> SEQUENCE: 4
ucgacgugca gcucg                                                    15